United States Patent
Lopez (10) Patent No.: US 12,281,974 B2
(45) Date of Patent: Apr. 22, 2025

(54) AIR QUALITY AND PARTICULATE DETECTION SYSTEM

(71) Applicant: Carrier Corporation, Palm Beach Gardens, FL (US)

(72) Inventor: Raul Perez Lopez, Esplugues de Llobregat (ES)

(73) Assignee: CARRIER CORPORATION, Palm Beach Gardens, FL (US)

( * ) Notice: Subject to any disclaimer, the term of this patent is extended or adjusted under 35 U.S.C. 154(b) by 445 days.

(21) Appl. No.: 17/452,898

(22) Filed: Oct. 29, 2021

(65) Prior Publication Data

US 2022/0146397 A1     May 12, 2022

Related U.S. Application Data

(60) Provisional application No. 63/198,712, filed on Nov. 6, 2020.

(51) Int. Cl.
*G01N 15/06*     (2024.01)
*A61L 9/20*     (2006.01)
*G01N 15/075*     (2024.01)

(52) U.S. Cl.
CPC ............... *G01N 15/06* (2013.01); *A61L 9/20* (2013.01); *A61L 2209/12* (2013.01); *A61L 2209/14* (2013.01); *G01N 15/075* (2024.01)

(58) Field of Classification Search
CPC ............ G01N 15/06; G01N 15/075; G01N 2015/019; G01N 1/2273; G01N 15/1434;
(Continued)

(56) References Cited

U.S. PATENT DOCUMENTS 5,240,478 A * 8/1993 Messina ............... B01D 46/88
                                                55/471
7,151,264 B2    12/2006 Ehlers, Sr.
(Continued)

FOREIGN PATENT DOCUMENTS

CN        205428117 U    8/2016
DE    102009011846 B4    7/2015
(Continued)

*Primary Examiner* — Mohammad K Islam
(74) *Attorney, Agent, or Firm* — CANTOR COLBURN LLP (57) ABSTRACT

An air quality and particulate detection system comprising: an air quality and particulate detector comprising a particulate detection chamber in fluid communication via an orifice with an adjacent air quality member, the particulate detection chamber comprising a blower adjacent to a particle filter and a laser source, and the air quality member comprising a channel having substantially parallel sides for operably coupling a HEPA filter adjacent and substantially parallel to the orifice, and for operably coupling one or more ultraviolet light emitting diodes (LEDs) downstream from the HEPA filter, and an exhaust pipe for returning treated air to a protected area; one or more pipe runs fluidly connected to the particulate detection chamber, wherein each of the one or more pipe runs includes one or more sampling points configured to allow air particulate entry from the protected area, into at least one of the one or more pipe runs.

18 Claims, 5 Drawing Sheets

(58) Field of Classification Search
CPC ....... G01N 15/1459; G01N 2001/2223; G01N 2001/245; G01N 2015/0046; G01N 2015/1486; G01N 1/2205; G01N 15/0205; G01N 15/0211; A61L 9/20; A61L 2209/12; A61L 2209/14; F24F 8/22; F24F 2110/50; F24F 2110/64; Y02B 30/70

See application file for complete search history.

(56) References Cited

U.S. PATENT DOCUMENTS

| | | | |
|---|---|---|---|
| 9,791,354 | B2 | 10/2017 | Koester |
| 9,993,828 | B2 | 6/2018 | Ajay et al. |
| 10,545,041 | B2 | 1/2020 | Ajay et al. |
| 10,677,705 | B2 | 6/2020 | Cooper et al. |
| 10,690,584 | B2 | 6/2020 | Burriel et al. |
| 2004/0045342 | A1* | 3/2004 | Jones ............ G01N 1/2205 422/123 |
| 2008/0286163 | A1* | 11/2008 | Garfield ............ A61L 9/205 427/532 |
| 2009/0123343 | A1* | 5/2009 | Kwiatkowski ..... B01D 53/8668 210/504 |
| 2009/0252654 | A1* | 10/2009 | Hsu ................ A61L 9/205 422/122 |
| 2012/0067143 | A1* | 3/2012 | Griffin ............ G01N 1/28 73/863.23 |
| 2012/0199003 | A1* | 8/2012 | Melikov ............ G16H 50/80 454/192 |
| 2013/0055692 | A1* | 3/2013 | Cecchi ............ B01D 46/44 55/342 |
| 2015/0033942 | A1* | 2/2015 | Zhang ............ B01D 53/0454 96/108 |
| 2017/0016638 | A1 | 1/2017 | Yun |
| 2018/0003612 | A1* | 1/2018 | Cole ............ G01N 15/1434 |
| 2018/0154297 | A1 | 6/2018 | Maletich |
| 2018/0363935 | A1 | 12/2018 | Lakamraju et al. |
| 2019/0145883 | A1* | 5/2019 | Burriel ............ G01N 15/1436 250/435 |
| 2020/0061231 | A1* | 2/2020 | Jeong ............ B01D 46/64 |
| 2021/0356153 | A1* | 11/2021 | Nesler ............ F24F 11/46 |
| 2021/0393841 | A1* | 12/2021 | Vandyke ............ B64D 13/06 |
| 2022/0105457 | A1* | 4/2022 | Knappenberger . B01D 39/1623 |

FOREIGN PATENT DOCUMENTS

| | | |
|---|---|---|
| EP | 1739405 A1 | 1/2007 |
| EP | 3483585 A1 | 5/2019 |
| TW | 200507925 A | 3/2005 |

* cited by examiner

AIR QUALITY AND PARTICULATE DETECTION SYSTEM

CROSS REFERENCE TO A RELATED APPLICATION

The application claims the benefit of U.S. Provisional Application No. 63/198,712 filed Nov. 6, 2020, the contents of which are hereby incorporated in their entirety.

BACKGROUND

The subject matter disclosed herein generally relates to the field of air quality and particulate detection, and more specifically, a system and method for detecting air particulate and improving air quality utilizing aspiration and ultraviolet germicidal irradiation.

Aspirating smoke detection systems provide early alarm on smoke generation in the protected areas by actively draw air from a protected area into a sampling chamber before returning the detected air to the protected area, generating an air recirculation. Typically, an aspirated smoke detection system continuously draws in air samples from several intake points of a pipe system, analyzes the air particulate content and returns the sampled air back to a protected area. A range of air particulates may be present, such as combustion materials, oil mist, metallic powders and microorganisms. Prior to returning the detected air to the protected area, it may be desirable to treat the air to remove airborne microorganisms.

BRIEF SUMMARY

According to one embodiment, an air quality and particulate detection system including: an air quality and particulate detector comprising a particulate detection chamber in fluid communication via an orifice with an adjacent air quality member, the particulate detection chamber including a blower adjacent to a particle filter and a laser source, and the air quality member including: a channel having substantially parallel sides for operably coupling a HEPA filter adjacent and substantially parallel to the orifice, and for operably coupling one or more ultraviolet light emitting diodes (LEDs) downstream from the HEPA filter, and an exhaust pipe for returning treated air to a protected area; and one or more pipe runs fluidly connected to the particulate detection chamber, wherein each of the one or more pipe runs includes one or more sampling points configured to allow air particulate entry from the protected area, into at least one of the one or more pipe runs.

In addition to one or more of the features described above, or as an alternative, further embodiments, the air quality and particulate detection system further including one or more secondary particulate detectors fluidly connected to the air quality and particulate detector through the one or more pipe runs.

In addition to one or more of the features described above, or as an alternative, further embodiments, the air quality and particulate detection system wherein the HEPA filter has a designation equal to or greater than MERV 6 and equal to or less than MERV 18.

In addition to one or more of the features described above, or as an alternative, further embodiments, the air quality and particulate detection system wherein the ultraviolet LEDs generate light in wavelength range equal to or greater than 200 nm and equal to or less than 320 nm.

In addition to one or more of the features described above, or as an alternative, further embodiments, the air quality and particulate detection system wherein the blower is adjacent to a particle filter and a laser source, the laser source configured to generate a laser having a plurality of wavelengths.

In addition to one or more of the features described above, or as an alternative, further embodiments, the air quality and particulate detection system wherein the laser source is adjacent to a sensor, the sensor configured to detect at least one of an amount of laser scatter and laser fluorescence in response to interaction of the laser and air particulates.

In addition to one or more of the features described above, or as an alternative, further embodiments, the air quality and particulate detection system wherein the blower is adjacent to: an infrared light source configured to generate an infrared light, and to a sensor configured to detect an infrared signature of an air particulate in response to interaction of the infrared light and the air particulate.

In addition to one or more of the features described above, or as an alternative, further embodiments, the air quality and particulate detector is configured to determine an identity of the air particulate in response to at least one of an amount of light scatter and the laser fluorescence.

In addition to one or more of the features described above, or as an alternative, further embodiments, the air quality and particulate detection system wherein the air quality and particulate detector is configured to activate an alarm in response to the identity of the air particulate.

In addition to one or more of the features described above, or as an alternative, further embodiments, the air quality and particulate detection system wherein the air quality and particulate detector is configured to transmit the infrared signature to the air quality and particulate detection system.

In addition to one or more of the features described above, or as an alternative, further embodiments, the air quality and particulate detection system wherein the air quality and particulate detector is configured to activate an alarm in response to the identity of the air particulate.

According to one embodiment, an air quality and particulate detector including: an air quality and particulate detector including a particulate detection chamber in fluid communication via an orifice with an adjacent air quality member wherein the particulate detection chamber comprises a blower adjacent to a particle filter and a laser source, and the air quality member comprises a channel having substantially parallel sides for operably coupling a HEPA filter adjacent and substantially parallel to the orifice, and for operably coupling one or more ultraviolet light emitting diodes (LEDs) upstream from the HEPA filter, and an exhaust pipe for returning treated air to a protected area.

In addition to one or more of the features described above, or as an alternative, further embodiments, the air quality and particulate detector wherein the HEPA filter has a designation equal to or greater than MERV 6 and equal to or less than MERV 18.

In addition to one or more of the features described above, or as an alternative, further embodiments, the air quality and particulate detector, wherein the ultraviolet LEDs generate light in the wavelength range of 200 to 320 nm.

In addition to one or more of the features described above, or as an alternative, further embodiments, the air quality and particulate detector wherein the blower is adjacent to at least one of a particle filter and a laser source, the laser source configured to generate a laser having a plurality of wavelengths.

In addition to one or more of the features described above, or as an alternative, further embodiments, the air quality and particulate detector wherein the laser source is adjacent to a sensor, the sensor configured to detect at least one of an amount of laser scatter and laser fluorescence in response to interaction of the laser and air particulates.

According to one embodiment, a method of operating an air quality and particulate system, the method including: allowing air particulate entry from an airflow of a protected area into one or more pipe runs through one or more sampling points in the airflow, wherein each of the one or more pipe runs initiate at a first end and terminate at a second end; conveying the air particulate in the airflow from the second end to a particulate detection chamber of an operably coupled air quality and particulate detector; detecting the air particulate in the particulate detection chamber and separating the air particulate from the airflow; conveying the airflow through a particulate detection chamber orifice and through a HEPA filter positioned in an adjacent air quality member; treating the airflow in the air quality member, with ultraviolet germicidal radiation from one or more ultraviolet light emitting diodes (LEDs); and returning the airflow to the protected area via an exhaust pipe.

In addition to one or more of the features described above, or as an alternative, further embodiments, the method of operating an air quality and particulate system wherein the HEPA filter has a designation equal to or greater than MERV 6 and equal to or less than MERV 18.

In addition to one or more of the features described above, or as an alternative, further embodiments, the method of operating an air quality and particulate system wherein the one or more LEDs generate light in the wavelength range of 200 to 320 nm.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION

The following descriptions should not be considered limiting in any way. With reference to the accompanying drawings, like elements are numbered alike.

DETAILED DESCRIPTION

A detailed description of one or more embodiments of the disclosed system and method are presented herein by way of exemplification and not limitation with reference to the Figures.

Detector units, such as optical fire detectors, gas detectors, etc., are used to detect a fire characteristic. An aspirated smoke detector is one type of fire detector that uses a suction unit, such as a blower or fan, that draws in air from the protected area. Typically, an aspirated smoke detection system continuously draws in air samples from several intake points of a pipe system, and analyzes the air particulate content. A range of air particulates may be present, such as combustion materials, oil mist, metallic powders, and microorganisms including bacteria, viruses, fungi, prions, viroid and spores. If a fire characteristic is recognized by a detector unit connected to the pipe system, an alarm is generally activated. However, if microorganisms are present in the air, they may be returned to the protected space untreated and potentially cause harm to building occupants. Described below is an air quality and particulate detection system that detects of the presence of air particulates and removes and/or treats harmful microorganisms from the environmental background using optical scattering, and at least one of a filter media and ultraviolet light before returning the air to a protected area.

Figure 1:
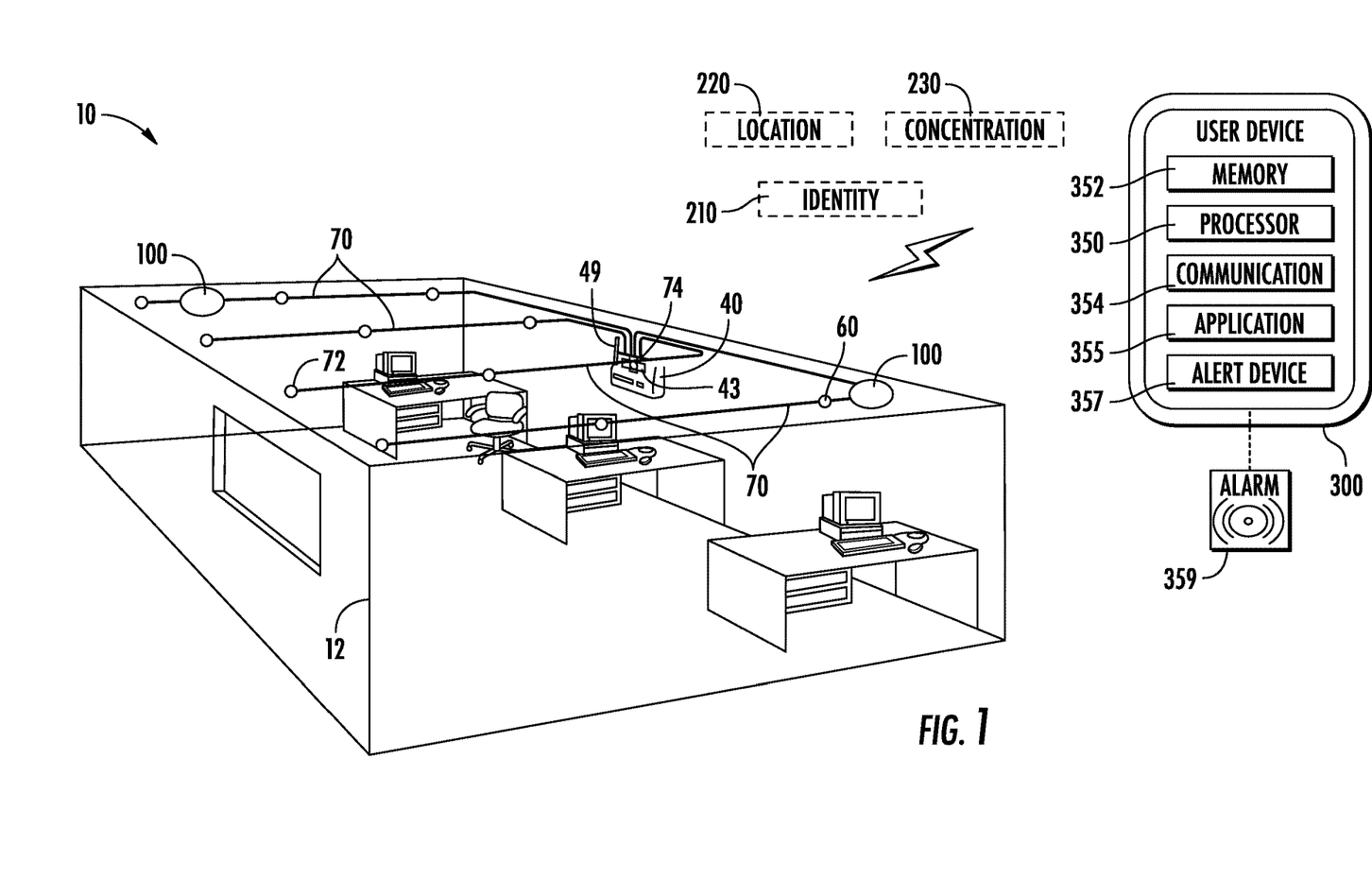
FIG. 1 is a schematic illustration of an air quality and particulate detection system, in accordance with an embodiment of the disclosure.

Referring now to FIG. 1, FIG. 1 shows a schematic illustration of an air quality and aspirated particulate detection system 10, according to an embodiment of the present disclosure. The air quality and aspirated particulate detection system 10 includes an air quality and particulate detector 40, one or more pipe runs 70 fluidly connected to the air quality and particle detector 40. The air quality and aspirated particulate detection system 10 may also include one or more secondary particulate detectors 100 fluidly connected to the air quality and particulate detector 40 through the one or more pipe runs 70. Each of the one or more pipe runs 70 initiate at a first end 72 and terminates at a second end 74. The air quality and particulate detector 40, further described below, is fluidly connected to each of the one or more pipe runs 70 at the second end 74. Each of the one or more pipe runs 70 includes one or more sampling points 60 configured to allow air particulates entry into at least one of the one or more pipe runs. The sampling points 60 may be an orifice and/or a nozzle in two non-limiting embodiments.

Figure 2:
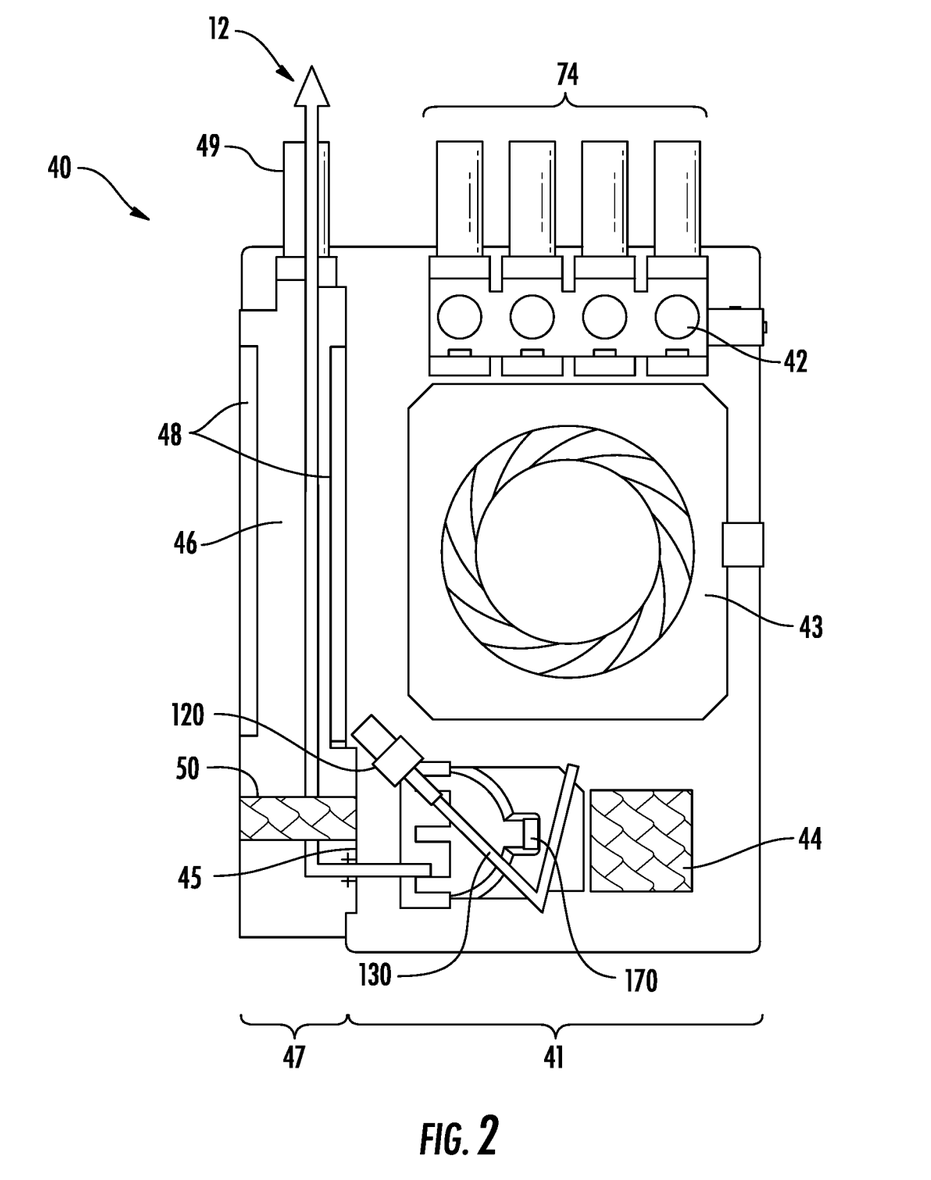
FIG. 2 is a cross-sectional illustration of an air quality and particulate detector of FIG. 1, in accordance with an embodiment of the disclosure.
Figure 3:
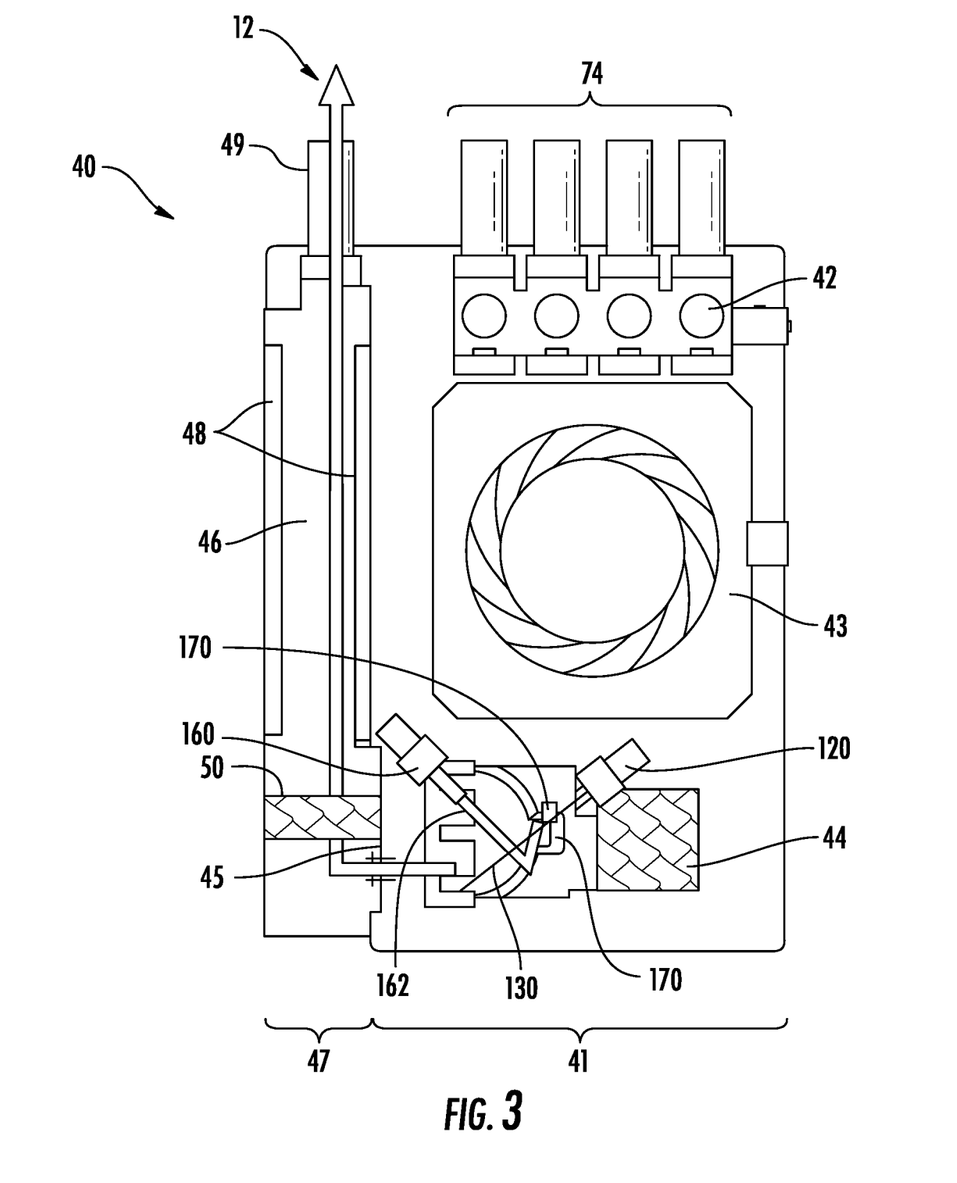
FIG. 3 is a cross-sectional illustration of an air quality and particulate detector of FIG. 1, in accordance with an embodiment of the disclosure.

Turning to FIG. 2 and FIG. 3, with reference to FIG. 1, FIGS. 2 and 3 each show a cross-section illustration of alternate embodiments of the air quality and particulate detector 40. The air quality and particulate detector 40 includes a particulate detection chamber 41, and an adjacent air quality member 47. The particulate detection chamber 41 is in airflow communication with the second end 74 of the one or more pipe runs 70, via one or more flow sensors 42. A blower 43 draws air through the one or more flow sensors 42 into the particulate detection chamber 41. Additionally, the blower 43 transports air particulates from each of the one or more sampling points 60 through the one or more pipe runs 70 to the second end 74, and into the particulate detection chamber 41. The blower 43 also transports the air particulates through each of the secondary particulate detectors 100. The blower 43 is adjacent to at least one of a media filter for removing particles such as dust, and other particles that are generally larger in size than a microorganism ("particle filter") 44, and a laser source 120, each located in the particulate detection chamber 41.

The laser source 120 may be configured to generate a laser 130 having a plurality of wavelengths and polarizations. The particulate detection chamber 41 may also include a sensor 170 adjacent to the laser source 120, the sensor configured to detect at least one of an amount of laser scatter, laser fluorescence or light generated from nonlinear optical effects in response to interaction of the laser 130 and air particulates. The air quality and particulate detector 40 may also be configured to determine an identity 210 of the air particulate in response to at least one of the amount of light scatter and the laser fluorescence. For example, light scatter and/or laser fluorescence may help identify smoke and combustion materials. Once the identity 210 of the air particulate is determined, the air quality and particulate detector 40 is configured to activate an alarm 359 in response to the identity 210 of the air particulate. The alarm may be audible and/or visual.

As illustrated in FIG. 3, the air quality and particulate detector 40 may also include a light source 160 configured to generate an ultraviolet light and/or an infrared light. The infrared light can be one or more wavelengths in a range of 700 nm to 30,000 nm, 700 nm to 4,000 nm, or more specifically, 700 nm to 1,500 nm. The ultraviolet light can be in a wavelength range of 25 nm to 480 nm, 160 nm to 480 nm or more specifically 375 nm to 480 nm. In addition, a sensor 170 may be configured to detect an ultraviolet or infrared signature of an air particulate in response to interaction of the infrared light 162 and the air particulate. The air quality and particulate detector 40 may be configured to reflect light from the light source 160 to the sensor 170. A single reflection, as shown in FIG. 3, increases the path length and improves sensitivity to the air particulates of interest. Multiple passes can be utilized to increase the path length further to improve sensitivity to gases. Ultraviolet light may be utilized to identify microorganisms by looking for laser induced fluorescence. Infrared may be utilized to detect combustion, industrial and toxic particulates that have vibrational resonances in the infrared frequency band. The resonance causes light to be absorbed reducing the transmitted light and changing the signal that the sensor 170 observes.

The air quality and particulate detector 40 may also be configured to determine an identity of 210 of an air particulate in response to the ultraviolet or infrared signature. A location 220, a concentration 230, and/or an identity 210 of the air particulate may be determined by algorithms that process the data collected from sensor 170 in the air quality and particulate detector 40. The location 220 may depict the protected area 12 where the air particulate was detected. The air particulate concentration 230 may depict a concentration of the air particulate in the location 220 and/or the protected area 12. The air particulate concentration 230 may be a particulate concentration at a size. In order to determine the location 220, the concentration 230, and/or the identity 210 of the air particulate, data collected by the air quality and particulate detector 40 may be compared to histogram values. The presence of a statistically significant value may initiate an alarm. The addition of multiple data points collected over time from different configures is used to identify the air particulates. A parallel decision-making approach based on support vector machine learning process compares the multiple data points to a multidimensional threshold. The result from the threshold is determination of the air particulates' identity 210. The air quality and particulate detector 40 can be configured to transmit the location 220, concentration 230, and/or identity 210 of the air particulate to a user device 300. An air particulate concentration 230, of the air particulate is then displayed on a user interface of a user device 300, an alarm panel and/or a remote visualization tool. A user device 300 may include but is not limited to a computing device, such as, for example, a desktop computer, a smart phone, a smart watch, a table, and/or any similar computing device known to one of skill in the art.

The user device 300 is in electronic communication with the air quality and particulate detector 40, and as discussed below may also be in electronic communication with one or more air particulate detectors 100. The user device 300 may include a touch screen (not shown), mouse, keyboard, scroll wheel, physical button, or any input mechanism known to one of skill in the art. The user device 300 may include a processor 350, memory 352 and communication module 354 as shown in FIG. 1. The processor 350 can be any type or combination of computer processors, such as a microprocessor, microcontroller, digital signal processor, application specific integrated circuit, programmable logic device, and/or field programmable gate array. The memory 352 is an example of a non-transitory computer readable storage medium tangibly embodied in the user device 300 including executable instructions stored therein, for instance, as firmware. The communication module 354 may implement one or more communication protocols as described in further detail herein. Embodiments herein generate a graphical user interface on the user device 300 through an application 355. The graphical user interface may display at least one of the air particulate concentration 230, the location 220 of the air particulate, and the identity 210 of the air particulate. The air quality and particulate detector 40 may be configured to activate an alarm 359 in response to the identity 210 of the air particulate. The alarm 359 may be audible and/or visual. The alarm 359 may emanate from the user device 300. The user device 300 may include an alert device 357 configured to activate the alarm 359. In three non-limiting examples, the alert device 357 may be a vibration motor, audio speaker, and/or display screen.

An orifice 45 permits air to flow from the particulate detection chamber 41 to the air quality member 47. In one non-limiting embodiment, the air quality member 47 includes a channel 46 having substantially parallel sides for operably coupling at least one filter media (e.g., a HEPA filter) 50 adjacent to the orifice 45, and one or more ultraviolet (UV) light emitting diodes (LEDs) 48 downstream from HEPA filter 50, and an exhaust pipe 49 downstream from the LEDs 48, for returning the airflow to the protected area 12. In another non-limiting embodiment, HEPA filter 50 may be positioned upstream of the LEDs 48 (not shown) and adjacent to the exhaust pipe. In yet another non-limiting embodiment, a HEPA filter 50 may be located at opposing ends of channel 46. The HEPA filter may be positioned transverse to channel 46, or in any orientation within the channel to accomplish adequate filtration.

The channel 46 may be manufactured in whole or in part, from a metal or metal alloy. The metal or metal alloy may have a reflective surface, such as galvanized steel, or polished aluminum. In some embodiments, the metal or metal alloy will be heat conductive so that heat generated by the LEDs 48 may be rejected to air. In some embodiments, the channel 46 may have a reflective lining, such as aluminum foil which also has good thermal conductive properties.

The HEPA filter 50 may be constructed from high efficiency particulate air (HEPA) filter material ("HEPA filter") having a range of MERV (minimum efficiency reporting value) ratings equal to or greater than MERV 6 and equal to or less than MERV 18, or more specifically, a rating range of MERV 10 to MERV 15, inclusive. By way of example, and not limitation a HEPA filter 50 having a minimum rating of MERV 13, is at least 85% effective at capturing particles ranging in size from 1 μm to 3 μm (micron). Higher MERV ratings (e.g., MERV 14) may capture a higher percentage of particles. HEPA filters are more than 99.97% efficient at filtering human-generated aerosols such as virus SARS- CoV-2 which ranges in size from approximately 0.6 μm to 0.14 μm, or the bacteria *S. aureus* (MRSA) which ranges in size from approximately to 0.10 μm 0.25 μm. When the HEPA filter 50 is combined with ultraviolet LEDs lighting 48 discussed below, the removal rate (RR) of microorganisms may increase based in part on the exposure of the air particulate to ultraviolet light over a period of time, such that the quality of the air returned to the protected space 12 is improved. The LEDs 48 may be of any shape, and may be arranged in the channel 46 in any pattern or configuration that provides the desired removal rate (RR). For example, LEDs may be one or more single LEDs, or an array, or may emit the same or differing light wavelengths. In one non-limiting embodiment, the LEDs 48 may be mounted on only one side of the channel 46. In another non-limiting embodiment, as illustrated in FIGS. 2 and 3, LEDs may be mounted on both sides of channel 46. In one non-limiting embodiment, LEDs 48 generate an ultraviolet light in a wavelength range of 200 to 280 nm (e.g., UVC). In another non-limiting embodiment, LEDs 48 generate ultraviolet light in a wavelength range of 280 nm to 320 nm (e.g., UVB). As air and particulates flow through channel 46, shortwave ultraviolet radiation from the LEDs can inactivate a microorganisms. For example, at wavelengths below 250 nm, UVC is also referred to as UVGI (ultraviolet germicidal irradiation) which can penetrate the outer structure of a cell and alter the DNA molecule, preventing replication and causing cell death. As used by Federal agencies such as OSHA, NIOSH and the CDC, the term UVGI refers more specifically to UVC wavelength between 253 to 254 nm.

Generally, UVGI systems, are rated to describe performance. For example, a UVGI Rating Value (URV) is based on the UV dose produced, which is defined by the product of exposure time and irradiance. By way of example, a URV 13 rating refers to a dose of UVGI of 20 J/m². Exposure time depends on airflow and the dimensions of the channel 46 (e.g., width, height, length) while irradiance depends on other factors described below. Exposure time ($E_t$) may be determined as follows:

$$E_t = Vol/Q = WHL/Q$$

where,
Vol=volume of the UV channel 46
Q=airflow, m³/s
WHL=width (W)*height (H)*length (L)

Assuming the flow through channel 46 is a turbulent mixture of air and particulates, the survival rate of any airborne microorganisms will be predicted by the standard exponential decay model, and the UVGI removal rate (RR) as follows: $RR = 1 - e^{-kI_mE_t}$ where,
RR=removal rate, fraction or % for a specific microorganism
k=UV rate constant, m²/J. This constant is related to the microorganism to be removed. For example, k for the SARS coronavirus is generally 0.01 m²/J.
$I_m$=mean irradiance, W/m².

The irradiance field as a function of distance from the LED axis is a product of the surface irradiance and the view factor, where the surface irradiance is determined by dividing the UV power output by the surface area of a lamp, such as LED 48.

The removal rate (RR) also considers the effect a diffuse enclosure may have in the total irradiation. For example, reflectivity and/or the length of channel 46 may be used to determine LED power. In general, reflectivity will increase the average irradiance while channel length will increase the average UV dose by increasing exposure time. By way of example, and not limitation, the UVGI RR for an air quality and particle detector 40 with a 6 liters/second airflow, the channel 46 may have the following dimensions: 30 cm (W)×30 cm (H)×30 cm (L) or an total volume of 30 cm³ to achieve approximately 4.5 seconds exposure time ($E_t$). The UVGI LED luminaire may be 25 cm (L), with diameter of approximately 5 cm. Considering the channel 46 has a specular surface, and a microorganism were approximately 15 cm from the LED luminaire, considering a 20 W lamp power output, the mean light irradiance at that distance would be 41.2 W/m². In this example, the UVGI removal rate (RR) would be 84% for SARS Coronavirus and 100% for Influenza.

In one non-limiting embodiment, the removal rate (RR) may be improved the when air quality and particulate detector 40 utilizes the HEPA filter 50 and UV LEDs 48 in combination. For example, assuming an initial particulate population of 1M of the bacteria *S. aureus* (MRSA), a filter having a rating of MERV 13 typically achieves a removal rate of approximately 85%, reducing to the bacterial population to approximately 150,000. As this remaining population flows through the orifice 45 to the channel 46, it is treated by the LEDs. Assuming the air quality and particulate detector 40 also meets a UVR 13 rating, after LED irradiation a removal rate of approximately 99.9% may be achieved. The total removal rate then, is approximately 99.985%, reducing the particulate population from approximately 1M to 150.

Figure 4:
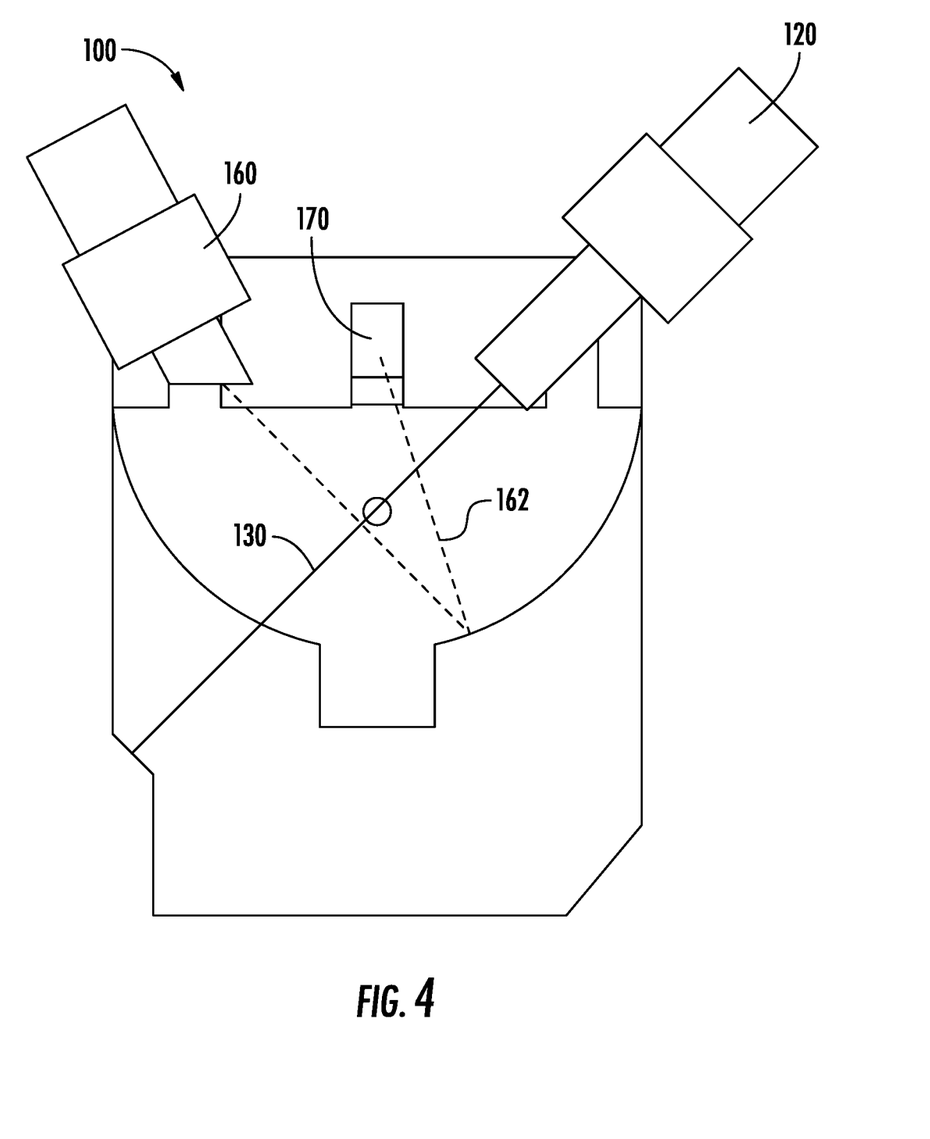
FIG. 4 is a cross-sectional illustration of a particulate detector of FIG. 1, in accordance with an embodiment of the disclosure.

Referring to FIG. 4, with continued reference to FIGS. 1-3, the air quality and aspirated particulate detection system 10 may include one or more secondary particulate detectors 100, which may be located proximate the first end of one of the pipe runs 70 or may be located in the middle of a pipe run 70. The secondary particulate detector 100 may be located proximate to at least one of the one or more sampling points 60. Advantageously, locating the secondary particulate detector 100 proximate to a sampling point 60 reduces detection time by removing transport time, air particulate identification occurs close to the sample point 60 rather than waiting for the air particulate to travel from the sampling point 60 through the pipe run 70 to the air quality and particulate detector 40. Also, advantageously, locating the secondary particulate detector 100 proximate to a sampling point 60 allows for identification of a location 220 of the air particulate. For example, a secondary particulate detector 100 may be located in each protected area 12 of a building and the protected area 12 where smoke arises may be identified by which the secondary particulate detector 100 detects smoke. The secondary particulate detector 100 may be in wireless electronic communication with the air quality and particulate detector 40 and may be powered by an independent power source (not shown), such as a battery.

The secondary particulate detector 100 may be located in the same protected area 12 as the air quality and particulate detector 40 as illustrated in FIG. 1, or they may be located in different protected areas. For example, the secondary particulate detector 100 may be located in a first protected area and the air quality and particulate detector 40 may be located in a second detection area separate from the first detection area. Advantageously, by locating the air quality and particulate detector 40 in a second detection area different from the first detection area, noise from the blower 42 may be reduced in the first protected area while maintaining quick particulate identification capability by the secondary particulate detector 100 in the first protected area.

The secondary particulate detector 100 may, similar to the air quality and particulate detector 40, include a laser source 120 configured to generate a laser 130 having a plurality of wavelengths and polarizations. The secondary particulate detector 100 may also include a sensor 170 adjacent to the laser source 120, the sensor configured to detect at least one of an amount of laser scatter, laser fluorescence or light generated from nonlinear optical effects in response to interaction of the laser 130 and air particulates. The secondary particulate detector 100 may also be configured to determine an identity 210 of the air particulate in response to at least one of the amount of light scatter and the laser fluorescence, and once the identity 210 of the air particulate is determined, may be configured to activate an alarm in response to the identity 210 of the air particulate. The alarm may be audible and/or visual. The secondary particulate detector 100 may also include a light source 160 configured to generate an ultraviolet light and/or an infrared light as described above.

As described above, the secondary particulate detector 100 may also be configured to determine an identity of 210 of an air particulate in response to the ultraviolet or infrared signature, such that a location 220, a concentration 230, and/or an identity 210 of the air particulate may be determined by algorithms that process the data collected from sensor 170. The secondary particulate detector 100 can also be configured to transmit the location 220, concentration 230, and/or identity 210 of the air particulate to a user device 300, each as described above.

Figure 5:
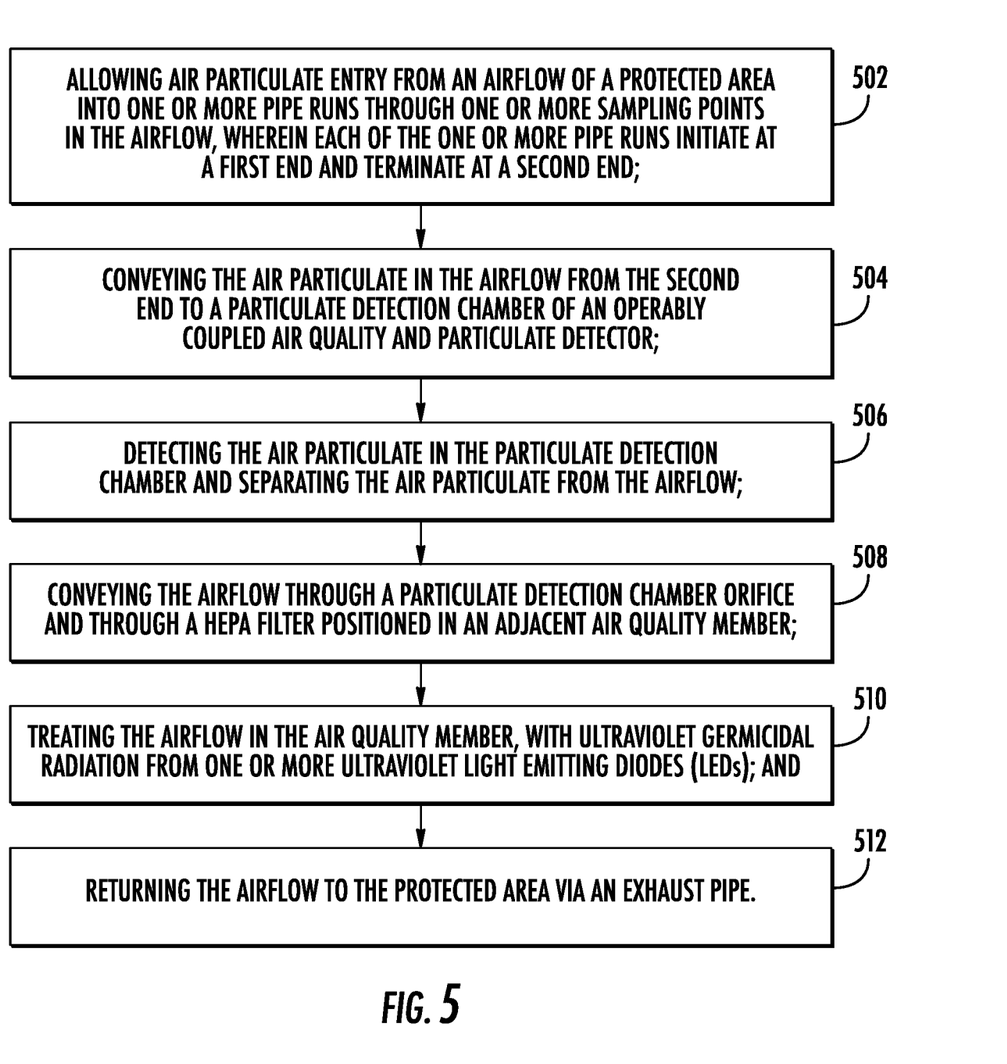
FIG. 5 is a flow diagram illustrating a method of detecting air particulates and improving air quality, according to an embodiment of the present disclosure.

Referring now to FIG. 5 with continued reference to FIGS. 1-4. FIG. 5 shows a flow diagram illustrating a method 500 of operating an air quality and particulate system, in accordance with embodiments of the disclosure. An air quality and particulate detection system 10 includes an air quality and particulate detector 40 (FIGS. 2, 3) comprising a particulate detection chamber 41 in fluid communication via an orifice 45 with an adjacent air quality member 47. The particulate detection chamber 41 may include a blower 43 adjacent to a particle filter 44 and a laser source 120. In some embodiments, the particulate detection chamber 41 may also include a blower 43 adjacent to an infrared light source 160 configured to generate an infrared light, and to a sensor 170 configured to detect an infrared signature of an air particulate in response to interaction of the infrared light and the air particulate. The air quality member includes a channel 46 having substantially parallel sides for operably coupling a HEPA filter 50 adjacent and substantially parallel to the orifice 45, and for operably coupling one or more ultraviolet light emitting diodes (LEDs) 48 upstream from the HEPA filter, and an exhaust pipe 49 for returning treated air to a protected area 12. One or more pipe runs 70 are fluidly connected to the particulate detection chamber 41. The one or more pipe runs includes one or more sampling points 60 configured to allow air particulate entry from the protected area 12, into at least one of the one or more pipe runs.

The method begins at 502 with allowing air particulate entry from an airflow of a protected area 12 into one or more pipe runs 70 through one or more sampling points 60 in the airflow, wherein each of the one or more pipe runs initiate at a first end 72 and terminate at a second end 74. At block 504, the method includes conveying the air particulate in the airflow from the second end 74 to the particulate detection chamber 41.

At block 506, the method includes detecting the air particulate in the particulate detection chamber and separating the air particulate from the airflow; In the particulate detection chamber 41, airflow and air particulates interact with the particulate filter 44. A portion of the particulate is separated from the airflow by the particulate filter 44. In general, the particulate filter is not a HEPA filter.

At block 508, the method includes conveying the airflow through a HEPA filter 50. The channel 44 of the air quality member, may have one or more HEPA filters 50. In some embodiments, the air may flow through a HEPA filter 50 adjacent to the particulate detection chamber orifice 45 and/or it may flow through a HEPA filter 50 adjacent to the exhaust pip 49. In one non-limiting embodiment, the HEPA filter material has a MERV rating equal to or greater than MERV 6 and equal to or less than MERV 18, or more specifically, a rating range of MERV 10 to MERV 15, inclusive. In general, HEPA filters within the stated range can be highly efficient at removing microorganisms, including living and non-living biological entities (e.g., viruses) from an airflow, as described above.

At block 510, the method includes treating the airflow, which may include microorganisms such as living and non-living biological entities (e.g., viruses), with ultraviolet germicidal radiation from one or more light emitting diodes (LEDs) 48. The ultraviolet LEDs may be arranged in any manner so as to effectively treat the airflow. In one non-limiting embodiment, the one or more LEDs generate light in a wavelength range equal to or greater than 200 nm and equal to or less than 320 nm. At block 514, the method includes returning the airflow to the protected area 12 via the exhaust pipe 49.

While the above description has described the flow process of FIG. 5 in a particular order, it should be appreciated that unless otherwise specifically required in the attached claims that the ordering of the steps may be varied.

As described above, embodiments can be in the form of processor-implemented processes and devices for practicing those processes, such as a processor. Embodiments can also be in the form of computer program code containing instructions embodied in tangible media, such as network cloud storage, SD cards, flash drives, floppy diskettes, CD ROMs, hard drives, or any other computer-readable storage medium, wherein, when the computer program code is loaded into and executed by a computer, the computer becomes a device for practicing the embodiments. Embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into an executed by a computer, the computer becomes a device for practicing the embodiments. When implemented on a general-purpose microprocessor, the computer program code segments configure the microprocessor to create specific logic circuits.

The term "about" is intended to include the degree of error associated with measurement of the particular quantity based upon the equipment available at the time of filing the application. For example, "about" can include a range of ±8% or 5%, or 2% of a given value.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made, and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

The invention claimed is:

1. An air quality and particulate detection system, comprising:
   an air quality and particulate detector comprising a particulate detection chamber in fluid communication via an orifice with an adjacent air quality member, the particulate detection chamber comprising a blower, a particle filter, and a laser source, wherein the blower is adjacent to the particle filter and the laser source, and
   the air quality member comprising:
      one or more ultraviolet light emitting diodes (LEDs), a channel having substantially parallel sides for operably coupling a HEPA filter adjacent and substantially parallel to the orifice, and for operably coupling the one or more ultraviolet light emitting diodes (LEDs) downstream from the HEPA filter, and
      an exhaust pipe for returning treated air to a protected area; and
   one or more pipe runs fluidly connected to the particulate detection chamber, wherein each of the one or more pipe runs includes one or more sampling points configured to allow air particulate entry from the protected area, into at least one of the one or more pipe runs.

2. The air quality and particulate detection system of claim 1, further comprising one or more secondary particulate detectors fluidly connected to the air quality and particulate detector through the one or more pipe runs.

3. The air quality and particulate detection system of claim 1, wherein the HEPA filter has a designation equal to or greater than MERV 6 and equal to or less than MERV 18.

4. The air quality and particulate detection system of claim 1, wherein the ultraviolet LEDs generate light in wavelength range equal to or greater than 200 nm and equal to or less than 320 nm.

5. The air quality and particulate detection system of claim 1, wherein the laser source is configured to generate a laser having a plurality of wavelengths.

6. The air quality and particulate detection system of claim 5, wherein the laser source is adjacent to a sensor, the sensor configured to detect at least one of an amount of laser scatter and laser fluorescence in response to interaction of the laser and air particulates.

7. The air quality and particulate detection system of claim 5, wherein the blower is adjacent to: an infrared light source configured to generate an infrared light, and a sensor configured to detect an infrared signature of an air particulate in response to interaction of the infrared light and the air particulate.

8. The air quality and particulate detection system of claim 7, wherein the air quality and particulate detector is configured to determine an identity of the air particulate in response to at least one of an amount of light scatter and laser fluorescence.

9. The air quality and particulate detection system of claim 8, wherein the air quality and particulate detector is configured to activate an alarm in response to the identity of the air particulate.

10. The air quality and particulate detection system of claim 9, wherein the air quality and particulate detector is configured to transmit the infrared signature to the air quality and particulate detection system.

11. An air quality and particulate detector, comprising:
    an air quality and particulate detector comprising a particulate detection chamber in fluid communication via an orifice with an adjacent air quality member wherein,
       the particulate detection chamber comprises a blower, a particle filter, and a laser source, wherein the blower is adjacent to the particle filter and the laser source, and
       the air quality member comprises one or more ultraviolet light emitting diodes (LEDs), a channel having substantially parallel sides for operably coupling a HEPA filter adjacent and substantially parallel to the orifice, and for operably coupling the one or more ultraviolet light emitting diodes (LEDs) upstream from the HEPA filter, and an exhaust pipe for returning treated air to a protected area.

12. The air quality and particulate detector of claim 11, wherein the HEPA filter has a designation equal to or greater than MERV 6 and equal to or less than MERV 18.

13. The air quality and particulate detection system of claim 11, wherein the ultraviolet LEDs generate light in the wavelength range of 200 to 320 nm.

14. The air quality and particulate detection system of claim 11, wherein the laser source is configured to generate a laser having a plurality of wavelengths.

15. The air quality and particulate detection system of claim 14, wherein the laser source is adjacent to a sensor, the sensor configured to detect at least one of an amount of laser scatter and laser fluorescence in response to interaction of the laser and air particulates.

16. A method of operating an air quality and particulate system, the method comprising:
    allowing air particulate entry from an airflow of a protected area into one or more pipe runs through one or more sampling points in the airflow, wherein each of the one or more pipe runs initiate at a first end and terminate at a second end;
    conveying the air particulate in the airflow from the second end to a particulate detection chamber of an operably coupled air quality and particulate detector;
    detecting the air particulate in the particulate detection chamber and separating the air particulate from the airflow in the particulate detection chamber by a particle filter, wherein the particulate detection chamber comprises a blower, a particle filter, and a laser source, and wherein the blower is adjacent to the particle filter and the laser source;
    conveying the airflow through a particulate detection chamber orifice and through a HEPA filter positioned in an adjacent air quality member, the air quality member comprising one or more ultraviolet light emitting diodes (LEDs), a channel having substantially parallel sides for operably coupling the HEPA filter adjacent and substantially parallel to the orifice, and for operably coupling the one or more ultraviolet light emitting diodes (LEDs) downstream from the HEPA filter, and an exhaust pipe;

treating the airflow in the air quality member, with ultraviolet germicidal radiation from the one or more ultraviolet light emitting diodes (LEDs); and returning the airflow to the protected area via the exhaust pipe.

17. The method of claim 16, wherein the HEPA filter has a designation equal to or greater than MERV 6 and equal to or less than MERV 18.

18. The method of claim 16, wherein the one or more LEDs generate light in the wavelength range of 200 to 320 nm.

* * * * *